(12) United States Patent
Li et al.

(10) Patent No.: US 11,648,095 B2
(45) Date of Patent: May 16, 2023

(54) INTRA-ORAL SCANNING DEVICE

(71) Applicant: D4D Technologies, LLC, Richardson, TX (US)

(72) Inventors: Ye Li, Plano, TX (US); Gregory R. Basile, Dallas, TX (US); Rod A. Duncan, Lucas, TX (US); Justin G. Graham, Wylie, TX (US); Grant E. Kenworthy, Allen, TX (US); Henley S. Quadling, Dallas, TX (US); Mark S. Quadling, Plano, TX (US); Andrei Tchouprakov, Plano, TX (US); Lasse H. Toimela, Plano, TX (US)

(73) Assignee: D4D Technologies, LLC, Richardson, TX (US)

( * ) Notice: Subject to any disclaimer, the term of this patent is extended or adjusted under 35 U.S.C. 154(b) by 333 days.

(21) Appl. No.: 16/059,915

(22) Filed: Aug. 9, 2018

(65) Prior Publication Data
US 2019/0046302 A1 Feb. 14, 2019

Related U.S. Application Data

(60) Provisional application No. 62/543,557, filed on Aug. 10, 2017.

(51) Int. Cl.
| | |
|---|---|
| *A61C 9/00* | (2006.01) |
| *A61B 1/00* | (2006.01) |
| *A61B 5/00* | (2006.01) |
| *A61B 6/02* | (2006.01) |
| *A61B 1/24* | (2006.01) |

(Continued)

(52) U.S. Cl.
CPC ........ *A61C 9/0053* (2013.01); *A61B 1/00172* (2013.01); *A61B 5/0062* (2013.01); *A61B 5/0088* (2013.01); *A61B 5/4547* (2013.01); *A61C 9/006* (2013.01); *A61B 1/0684* (2013.01); *A61B 1/24* (2013.01); *A61B 5/1077* (2013.01); *A61B 6/022* (2013.01); *A61C 7/002* (2013.01)

(58) Field of Classification Search
CPC ..... A61C 9/0053; A61C 9/006; A61C 9/0066; A61C 9/0073; A61B 1/00172; A61B 1/00163; A61B 1/0684; A61B 1/24; A61B 1/00177; A61B 5/0062; A61B 5/0088; A61B 5/4547; A61B 5/4552; A61B 5/4542

See application file for complete search history.

(56) References Cited

U.S. PATENT DOCUMENTS

| | | | |
|---|---|---|---|
| 6,614,538 B1 * | 9/2003 | Basler ................ | A61C 13/0004 356/602 |
| 6,979,496 B2 | 12/2005 | Haymann et al. | |

(Continued)

FOREIGN PATENT DOCUMENTS

| | | |
|---|---|---|
| EP | 0345368 | 12/1989 |
| KR | 20110127950 | 11/2011 |

(Continued)

*Primary Examiner* — Jacqueline T Johanas
*Assistant Examiner* — Shannel Nicole Belk
(74) *Attorney, Agent, or Firm* — Scheef & Stone, LLP; Robin L. Barnes; John G. Fischer

(57) ABSTRACT

An intra-oral scanning device includes a light source and an optical system, and communicates with a display system. The device has a reduced form factor as compared to prior devices, and it provides for more efficient transmission and capture of images.

19 Claims, 11 Drawing Sheets

(51) Int. Cl.
*A61B 1/06* (2006.01)
*A61C 7/00* (2006.01)
*A61B 5/107* (2006.01)

(56) References Cited

U.S. PATENT DOCUMENTS

| | | |
|---|---|---|
| D547,458 S | 7/2007 | Haymann et al. |
| D554,757 S | 11/2007 | Haymann et al. |
| D555,792 S | 11/2007 | Haymann et al. |
| D558,345 S | 12/2007 | Witt |
| 7,342,668 B2 | 3/2008 | Quadling et al. |
| 7,355,721 B2 | 4/2008 | Quadling et al. |
| 7,573,583 B2 | 8/2009 | Quadling et al. |
| 7,646,550 B2 | 1/2010 | Rohaly et al. |
| 7,670,272 B2 | 3/2010 | Quadling et al. |
| 7,746,568 B2 | 6/2010 | Rohaiy et al. |
| 7,789,601 B2 | 9/2010 | Prince et al. |
| 7,819,591 B2 | 10/2010 | Rohaly et al. |
| 7,978,892 B2 | 7/2011 | Quadling et al. |
| 8,035,637 B2 | 10/2011 | Kriveshko |
| 8,144,336 B2 | 3/2012 | Quadling et al. |
| 8,215,956 B2 | 7/2012 | Dunne et al. |
| 8,345,257 B2 | 1/2013 | Bonnema et al. |
| 8,345,261 B2 | 1/2013 | Quadling et al. |
| 8,487,962 B2 | 7/2013 | Quadling et al. |
| 8,532,355 B2 | 9/2013 | Quadling et al. |
| 8,675,291 B2 | 3/2014 | Rohaly et al. |
| 9,066,772 B2 | 6/2015 | Tchouprakov et al. |
| 9,191,648 B2 | 11/2015 | Kriveshko et al. |
| 9,208,531 B2 | 12/2015 | Boerjes et al. |
| 9,245,374 B2 | 1/2016 | McQueston et al. |
| 9,262,864 B2 | 2/2016 | Rohaly et al. |
| 9,364,300 B2 | 6/2016 | Tchouprakov et al. |
| 9,539,070 B2 * | 1/2017 | Rubbert ................. A61B 1/045 |
| D780,182 S | 2/2017 | Klein et al. |
| 9,967,543 B2 | 5/2018 | Yun et al. |
| 10,277,884 B2 | 4/2019 | Lee et al. |
| 10,667,887 B2 | 6/2020 | Rohaly et al. |
| 10,739,131 B2 | 8/2020 | Chang et al. |
| 11,006,858 B2 | 5/2021 | Chang et al. |
| 11,030,741 B2 | 6/2021 | Chang et al. |
| 11,163,976 B2 | 11/2021 | Kriveshko et al. |
| 11,202,560 B2 | 12/2021 | Chang et al. |
| 2002/0045811 A1 * | 4/2002 | Kittrell ............... A61B 1/00096 600/407 |
| 2008/0240668 A1 * | 10/2008 | Miyata ................. H04N 9/3152 385/147 |
| 2009/0262311 A1 * | 10/2009 | Lin ...................... G03B 21/008 353/81 |
| 2010/0253773 A1 | 10/2010 | Oota et al. |
| 2013/0130191 A1 * | 5/2013 | Iio ........................ A61B 5/0066 433/29 |
| 2015/0018613 A1 * | 1/2015 | Hollenbeck .......... A61B 5/1079 600/109 |
| 2016/0220332 A1 | 8/2016 | Chang et al. |
| 2016/0328843 A1 * | 11/2016 | Graham ............... A61C 9/006 |
| 2017/0094254 A1 | 3/2017 | Lee et al. |
| 2018/0310825 A1 * | 11/2018 | Kakuma ............... A61B 1/247 |
| 2019/0046302 A1 * | 2/2019 | Li ........................ A61B 5/0062 |
| 2019/0090784 A1 | 3/2019 | Chang et al. |
| 2019/0216690 A1 | 7/2019 | Wang et al. |
| 2019/0247163 A1 * | 8/2019 | Wu ....................... A61C 9/0053 |
| 2020/0288959 A1 * | 9/2020 | Lahti .................... A61B 1/247 |
| 2020/0345471 A1 * | 11/2020 | Schmid ............. A61B 1/00172 |

FOREIGN PATENT DOCUMENTS

| | | |
|---|---|---|
| KR | 20150111122 | 10/2015 |
| KR | 20150111122 A | 10/2015 |
| KR | 101717284 | 3/2017 |
| KR | 101717284 B1 | 3/2017 |

* cited by examiner

INTRA-ORAL SCANNING DEVICE

BACKGROUND OF THE INVENTION

Technical Field

This disclosure relates generally to scanning devices.

Brief Description of the Related Art

It is known to provide an intra-oral scanner to enable a user to scan dental patients intra-orally. Such devices are used in a standalone scanner, or as part of a computer-aided design and manufacture (CAD/CAM) system. A CAD/CAM system typically uses dental CAD software executing on a laptop or desktop machine, optionally together with specialized milling machine hardware driven by machine control CAM software. The dentist first prepares a patient's damaged tooth anatomy (using standardized dental practices) to receive a dental restoration including, but not limited to, an inlay, an onlay, a veneer, a crown or a bridge. Once the preparation has been made, the dentist uses the scanner described and illustrated herein to capture a digital impression of a patient's dental anatomy. Once the digital impression has been captured the dentist is presented with an "initial proposal" restoration by the automated CAD software. This initial proposal preferably automatically selects an appropriate tooth anatomy, and it sizes it to fit onto the preparation and within the patient's existing "good" anatomy. This initial proposal is then customized by the dental professional, typically using specialized software tools to adjust and modify the design, with the goal of ultimately achieving an optimized design that fits into the patient's anatomy. Once the final 3D model of the tooth has been achieved, it is sent electronically to a milling machine (or third party), which then generates the actual restoration from the design.

While existing scanner devices provide satisfactory results, there remains a need for improvements in scanning speed and accuracy, as well as to reduce the size and weight of the device to thereby make it easier to use in practice.

BRIEF SUMMARY

An intra-oral scanning device is provided to more efficiently and accurately scan dental patients intra-orally. The device typically comprises a component of an optical impression system for computer-aided design (CAD) and manufacture (CAM) of dental restorations. In operation, the device is used for recording topological characteristics of teeth, dental impressions, or stone models by digital methods and for use in CAD/CAM of dental restorative prosthetic devices. According to this disclosure, various operating components in the device are configured and arranged so as to simplify the mechanical and electrical packaging and assembly, and accordingly the scanner is much more compact and easier to use as compared to prior art intra-oral scanners.

The foregoing has outlined some of the more pertinent features of the subject matter. These features should be construed to be merely illustrative.

BRIEF DESCRIPTION OF THE DRAWINGS

For a more complete understanding of the disclosed subject matter and the advantages thereof, reference is now made to the following descriptions taken in conjunction with the accompanying drawings, in which.

DETAILED DESCRIPTION

As noted above, the scanner of this disclosure is a handheld optical scanner that is designed to be placed in a patient's mouth to create an image (typically a 3D image) of the teeth after preparation for dental restoration. The following describes an embodiment of this scanner.

Figure 1:
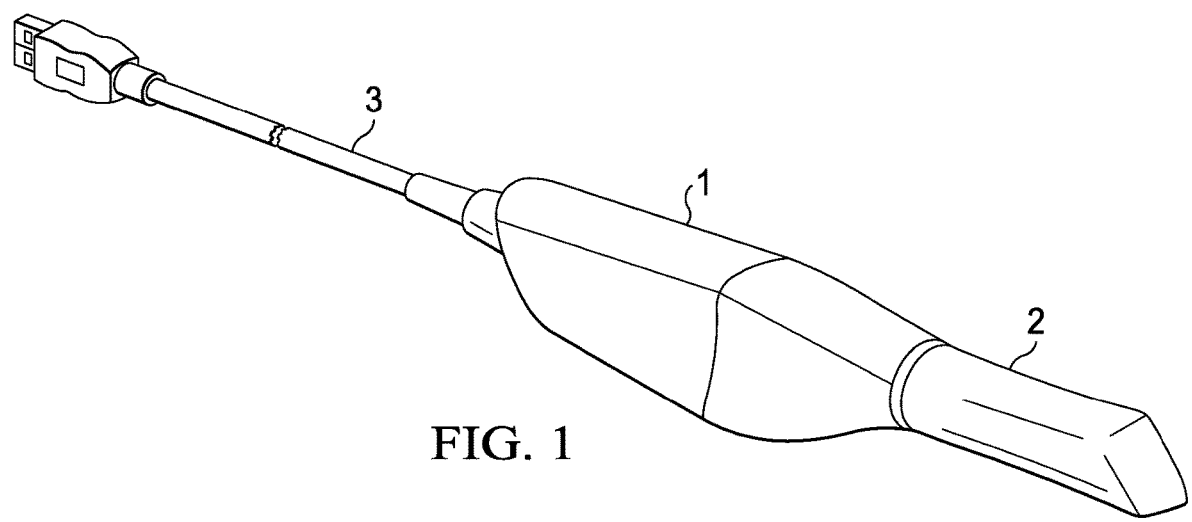
FIG. 1 depicts a perspective view of an embodiment of a hand-held scanner according to this disclosure.

In particular, FIG. 1 depicts a perspective view of the hand-held scanner in one embodiment. In this embodiment, the scanner preferably comprises a scanner body 1, a detachable scanner tip 2, and detachable data cable 3.

Figure 2:
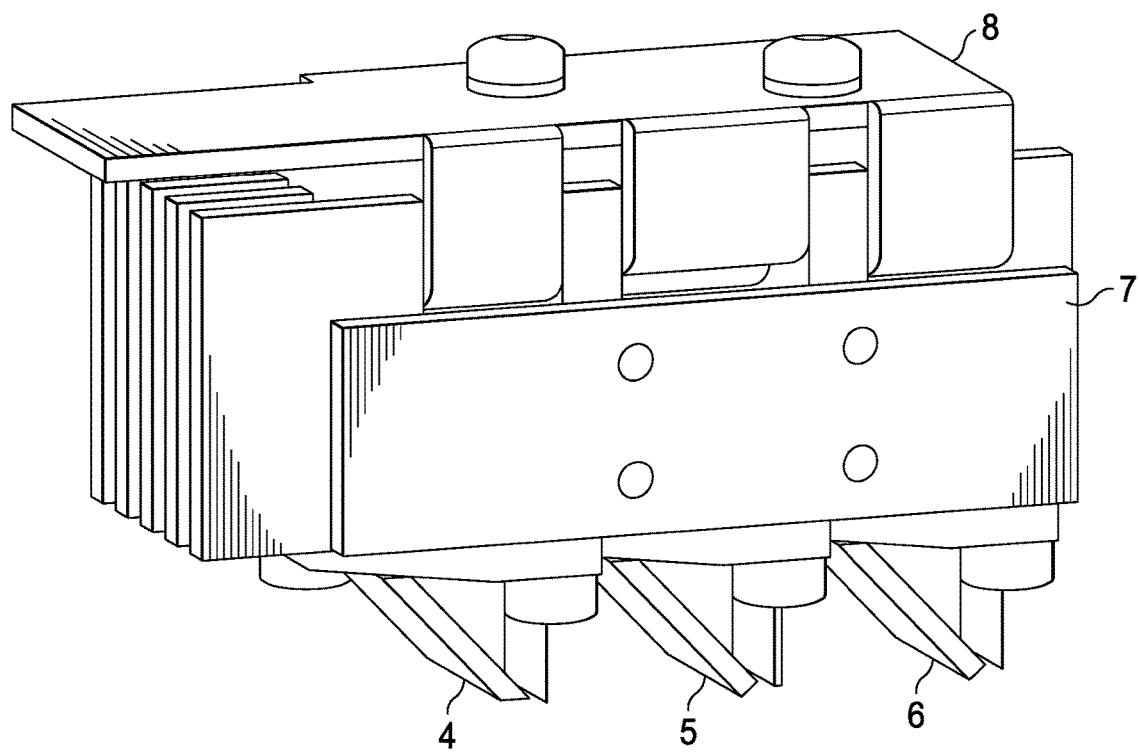
FIG. 2 depicts a light engine module of the scanner shown in a perspective view.
Figure 2A:
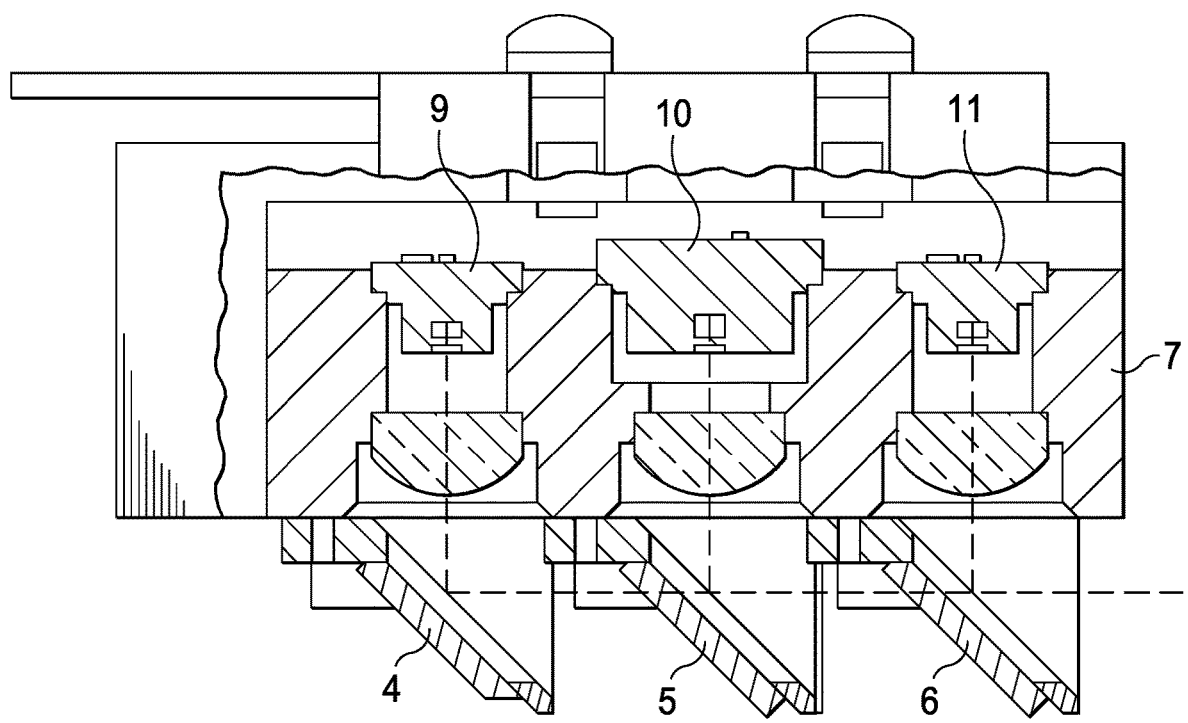
FIG. 2A depicts a cutaway (interior) view of the light engine module.

With reference now to FIG. 2, a light engine module of the scanner of FIG. 1 is shown in perspective, and FIG. 2A provides an interior (cutaway) view of the light engine module. The light engine module preferably comprises red laser diode 9, green laser diode 10, and blue laser diode 11. A full spectrum mirror 4, a red passing and green reflecting dichroic filter 5, and blue reflecting, red and green passing dichroic filter 6, respectively, are positioned adjacent the diodes. Element 7 is a laser housing and heat sink for the module, and element 8 is a laser flexible circuit board to which the laser diodes are mounted.

Figure 3:
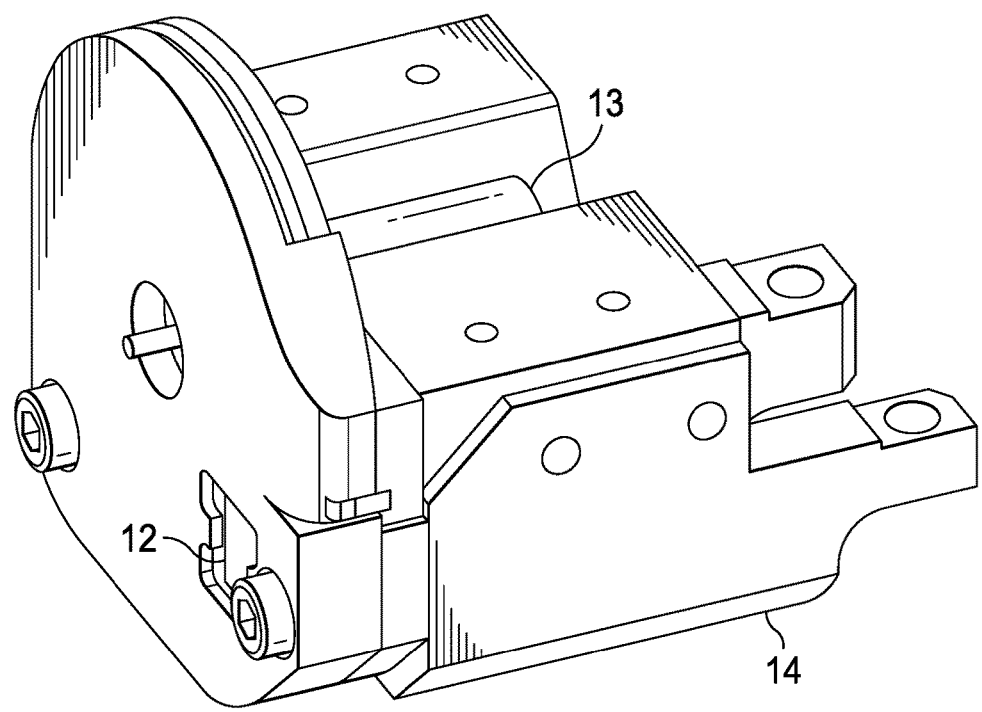
FIG. 3 depicts a despeckler module of the scanner in a perspective view.
Figure 3A:
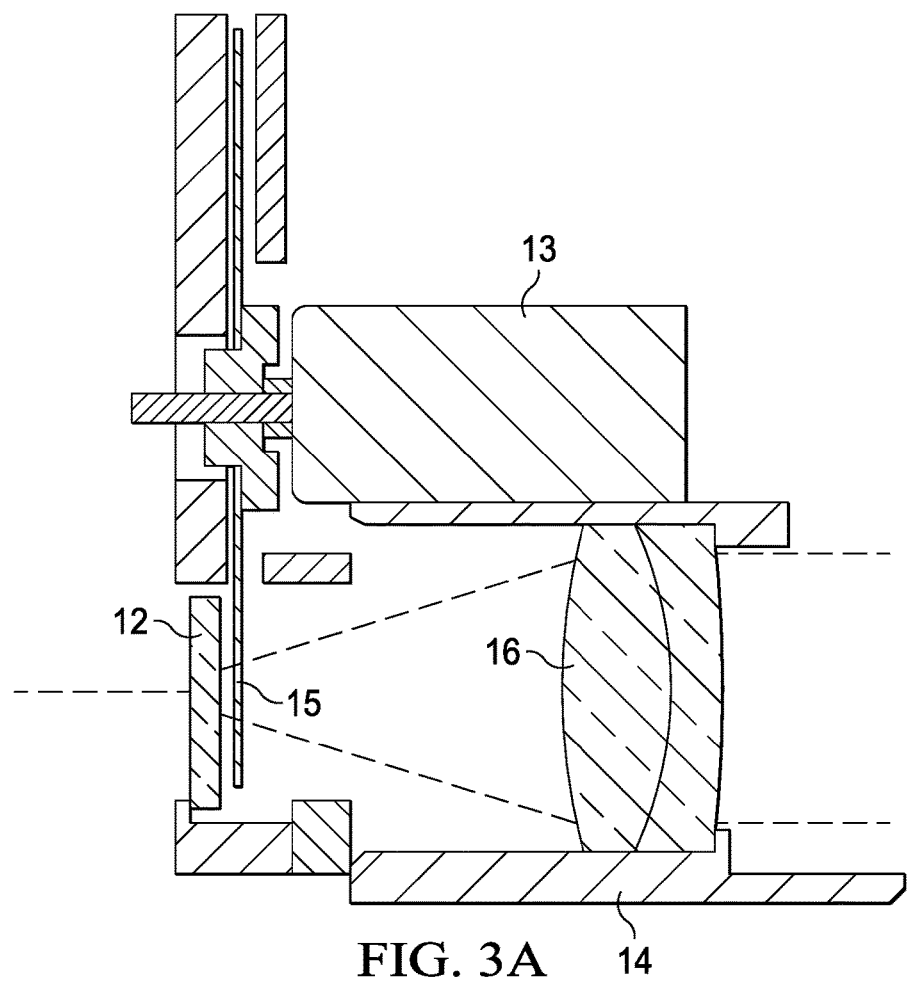
FIG. 3A depicts an interior view of the despeckler module.

FIG. 3 depicts a despeckler module, and FIG. 3A provides an interior view of the despeckler module. The despeckler module comprises micro lens array (MLA) 12, a despeckler drive motor 13, a despeckler housing 14, a diffuser disk 15 (that acts as a despeckling element), and an achromatic lens 16 (a "doublet" or "collimating" lens). The diffuser disk spins in front of the laser. In an alternative embodiment, the diffuser may move by other means in the vertical, horizontal, circular, or random axes.

Figure 4:
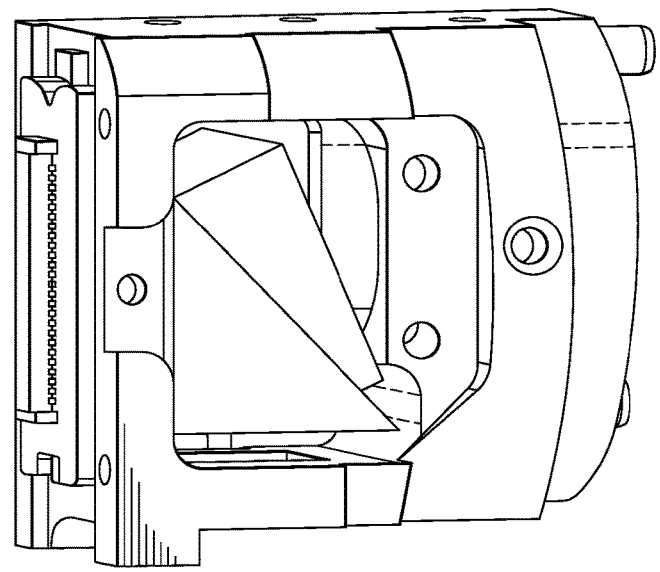
FIG. 4 depicts a light projection module of the scanner in a perspective view.
Figure 4A:
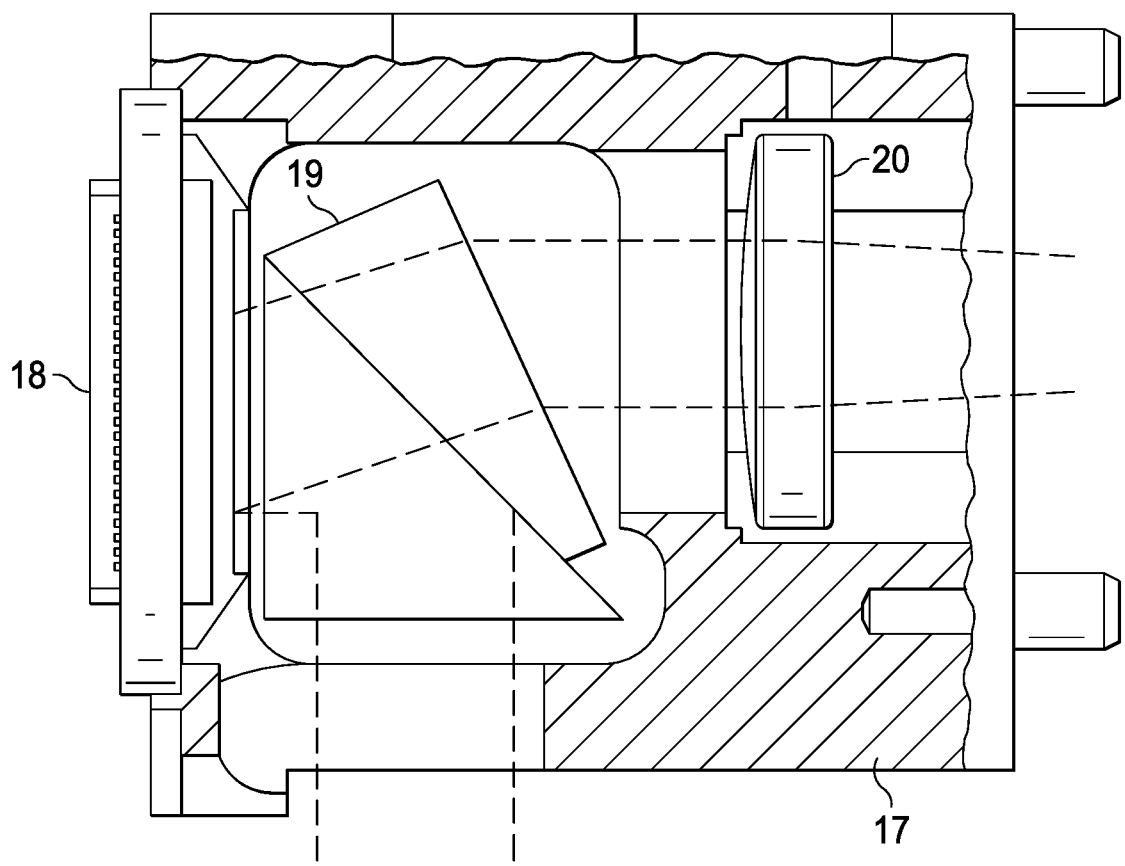
FIG. 4A depicts an interior view of the light projection module.

FIG. 4 depicts a projection module in perspective, and FIG. 4A depicts a cutaway view showing the light paths. As shown, the projection module comprises a TIR housing 17, a laser light spatial modulator chip 18 (Texas Instruments DLP® Technology), a Total Internal Reflection (TIR) prism 19, and a tele-centric lens 20. As depicted, the light comes into the module normal to the modulator chip surface; that light is then moved off-axis by the TIR prism 19. As will be described in more detail below, this configuration enables the size of the overall optics system to be substantially reduced, thereby enabling the overall scanner to be reduced in size.

Figure 5:
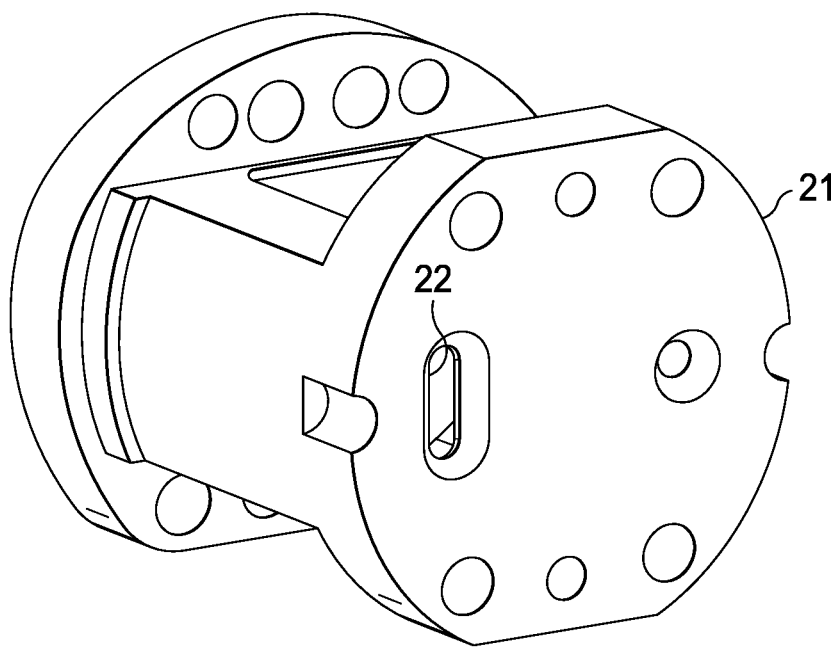
FIG. 5 depicts a lens tube module of the scanner in a perspective view.
Figure 5A:
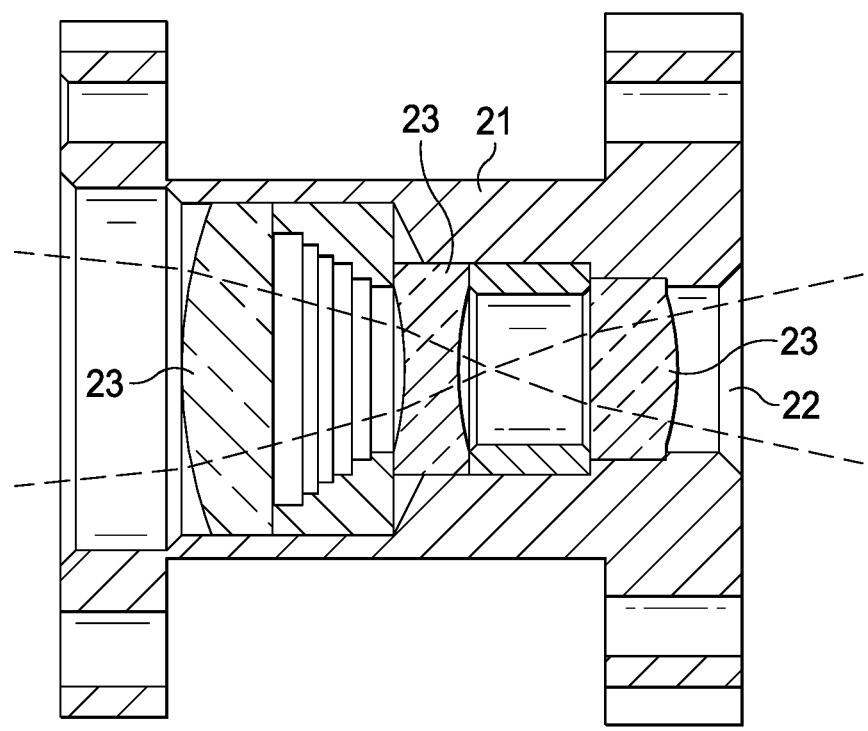
FIG. 5A depicts an interview of the lens tube module.

FIG. 5 depicts a lens tube module in perspective, and FIG. 5A depicts a cutaway view. As best seen in the perspective view, the module includes a magnification lens housing 21 (lens barrel) that includes a slotted (sometimes referred to herein as a "cat-eye") aperture 22. Magnification lenses 23 are supported substantially as shown. The aperture 22 provides significantly enhanced depth-of-field for the laser lines that comprise the projected image. In effect, and by using the aperture, the optics system sacrifices resolution in the vertical direction while significantly enhancing resolution in the horizontal direction. The notion here is to provide more optical power in the direction that matters to the imaging process.

Figure 6:
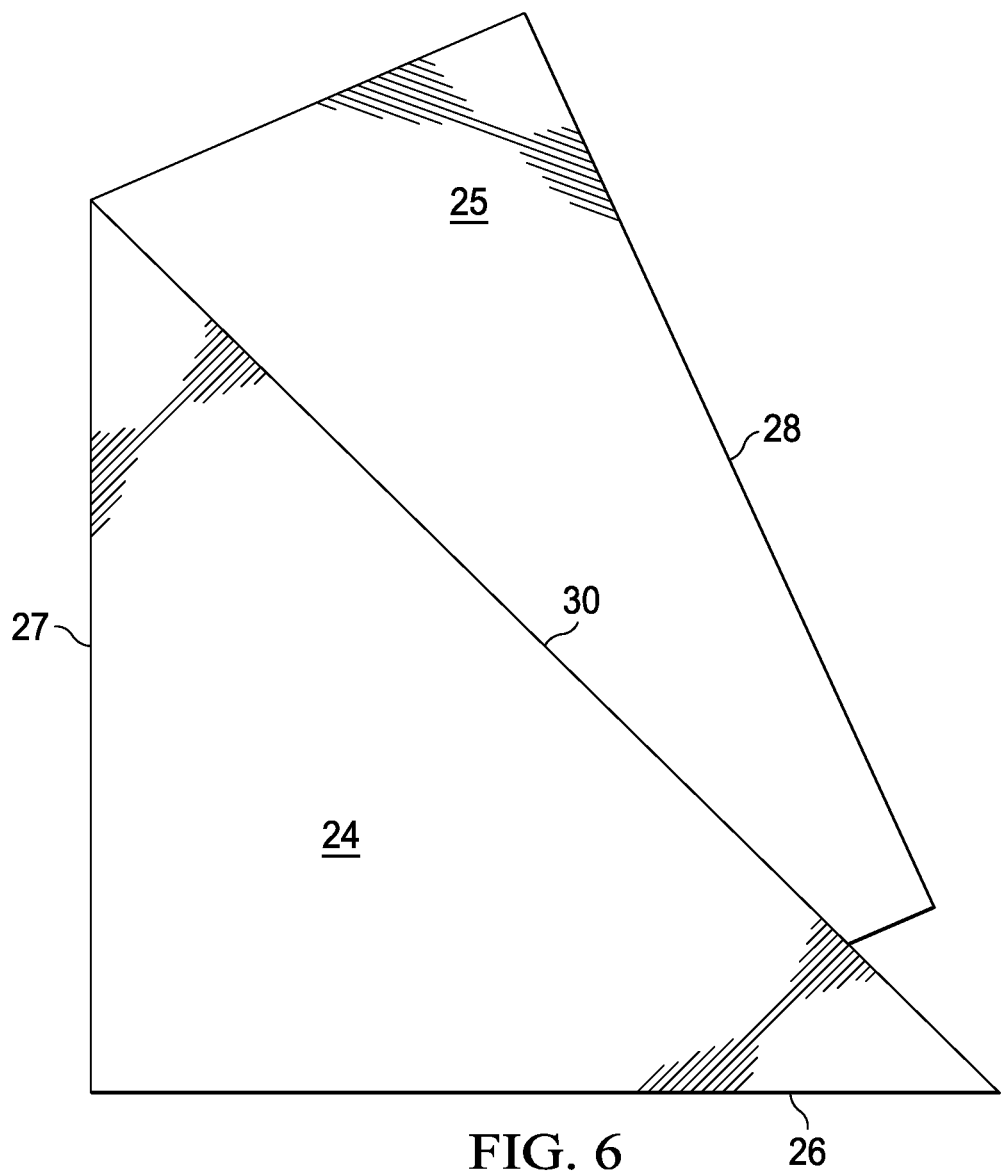
FIG. 6 depicts a preferred construction of the TIR prism in the light engine module of the scanner.
Figure 7A:
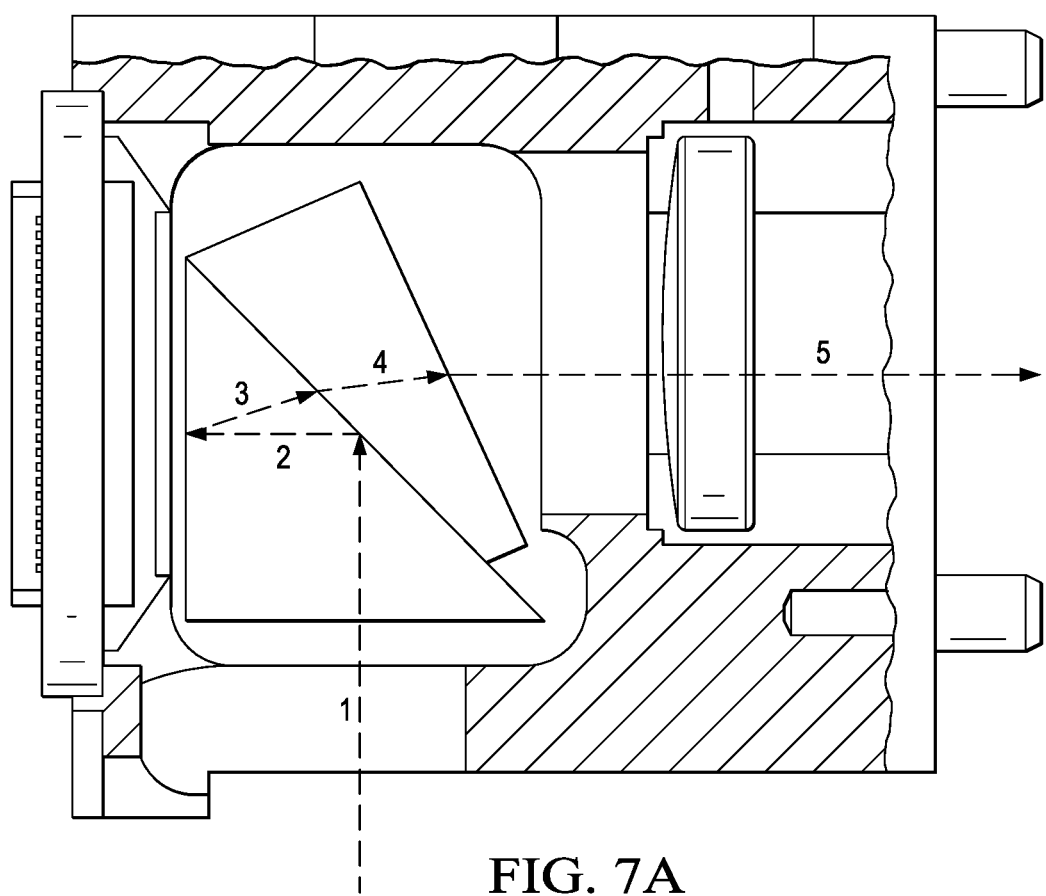
FIG. 7A depicts the beam path through the light engine module for light that is directed at greater than normal and thus projected to the rest of the optical system.
Figure 7B:
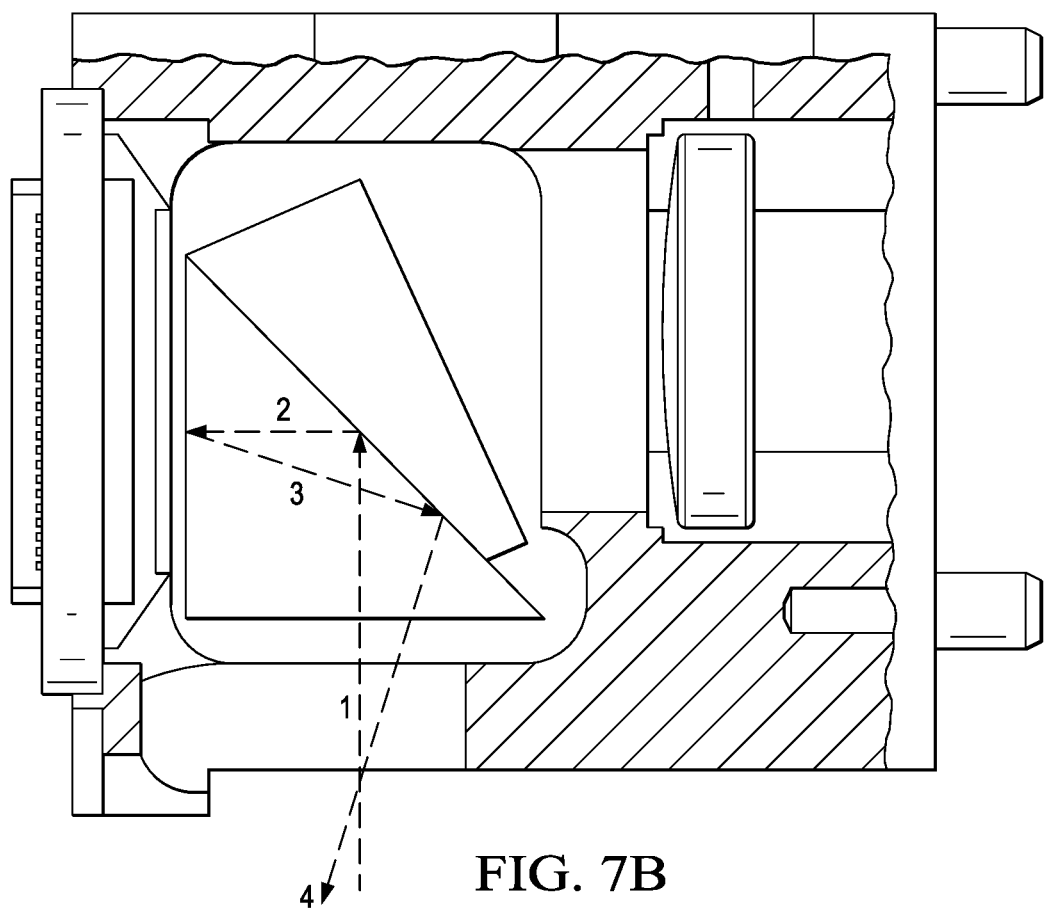
FIG. 7B depicts the beam path through the light engine module for light that is directed at less than normal and thus not projected.

The following provides additional details regarding the Total Internal Reflection (TIR) prism shown in FIG. 4, as well as its principle of operation. As depicted in FIG. 6, the TIR prism preferably is comprised of two pieces of glass, numbered 24 and 25, which pieces preferably are glued together with a very small air gap between them. The TIR prism is configured to transmit light that comes into the prism at a certain range of angles, and to reflect light that comes in at a different angle. This operation can be seen in FIG. 6 with respect to three (3) identified transmitting surfaces, as well as the TIR surface itself 30. As noted above, the TIR prism is used to transmit light of a certain incident angle and reflect light of a different incident angle. Light enters the prism at a normal to a first transmitting surface 26 and is largely reflected off of the TIR surface 30. This light is transmitted out of a second transmitting surface 27 onto a DMD surface 28, which will direct the light either at an angle greater than normal or less than normal depending in the DMD micro-mirrors' position. The light then again transits through the second transmitting surface 27. Light that exits the DMD surface 28 at an angle greater than normal is transmitted through the TIR surface 30 and is then transmitted out of the prism through a third transmitting surface 29. This is depicted in FIG. 7A. The third transmitting surface 29 is angled such that the exiting light is transmitted normal to the remaining projection path. Light that is reflected at an angle less than normal reflects off of the TIR surface 30 and is not projected through the system. This is depicted in FIG. 7B.

Thus, the TIR prism preferably is comprised of two prisms that are configured as shown, preferably with a few micron air gap there-between. The first prism 24 is a triangle (or right angle) prism comprising one angle at 90° and two other equal angles (at 45°), and it is formed of a material selected to ensure total internal reflection at surface 30. The second prism 25 is also a triangle prism, and it is formed in a shape of a wedge prism in which the wedge angle and material are designed to make the exiting laser beam parallel to the optical axis. Other than the 90° angle, the second prism has angles of approximately 21 and 69 degrees. As noted, preferably the prisms are bonded together with a small air gap along the surface 30. Preferably, the prisms are sized to ensure that there is a sufficient optically-clear aperture to cover the pattern size of laser beam. As noted above, the laser beam enters the first prism 24 at normal incident angle, and it is internally reflected (totally) by the 45° TIR surface 30 such that the beam then hits on the light modulator. When the modulator is turned on, and when each individual mirror turns +12 degree, then the laser beam is reflected back to prism 24 through to the 45° TIR surface 30. Due to the DMD angle, there is no internal reflection at the surface 30 of prism 24. Thus, the laser beam travels through the first prism and reaches the second prism 25, where it is then bent by the third transmitting (back) surface such that the laser beam is parallel to the optical axis and goes through to the rest of the optical path. As noted above, this operation is depicted in FIG. 7A. When the DMD is at a parked position of 0° degree or at OFF position of angle of −12° degree, the laser beam does not make it through the 45° surface 30 of the first prism due to total internal reflection.

The above-described manner of arranging the TIR configuration enables both the DMD chip and the CCD (or CMOS-based) chip to be positioned in a vertical plane, and it simplifies the mechanical and electrical packaging and assembly. In part due to this construction, the overall scanner is much more compact than prior devices of this type.

In an alternative embodiment, the relative positions of the two prisms are switched, in which case the exit laser beam is normal to the TIR surface of the 45° prism, and the DMD chip is in a horizontal plane and perpendicular to CCD (or CMOS) surface.

Figure 8A:
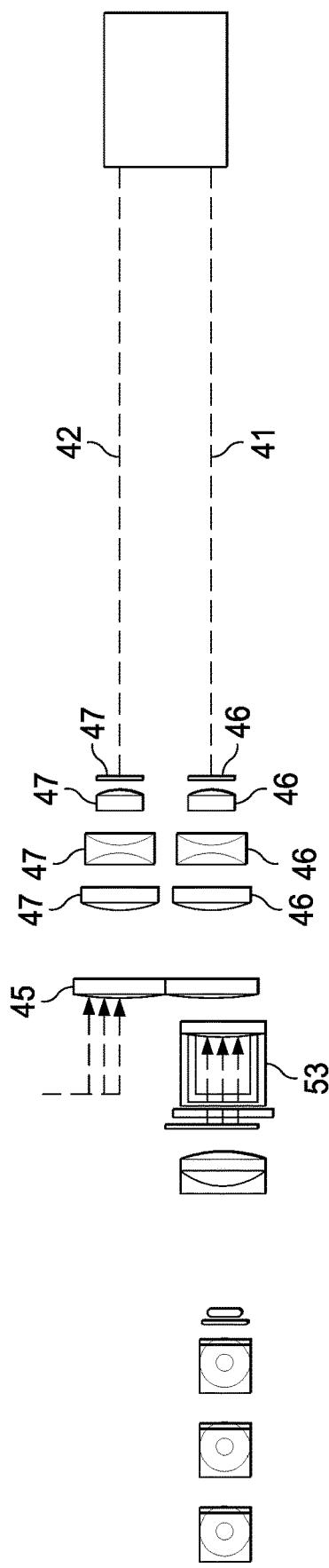
FIG. 8A is a plan view of the optical system of the scanner.
Figure 8B:
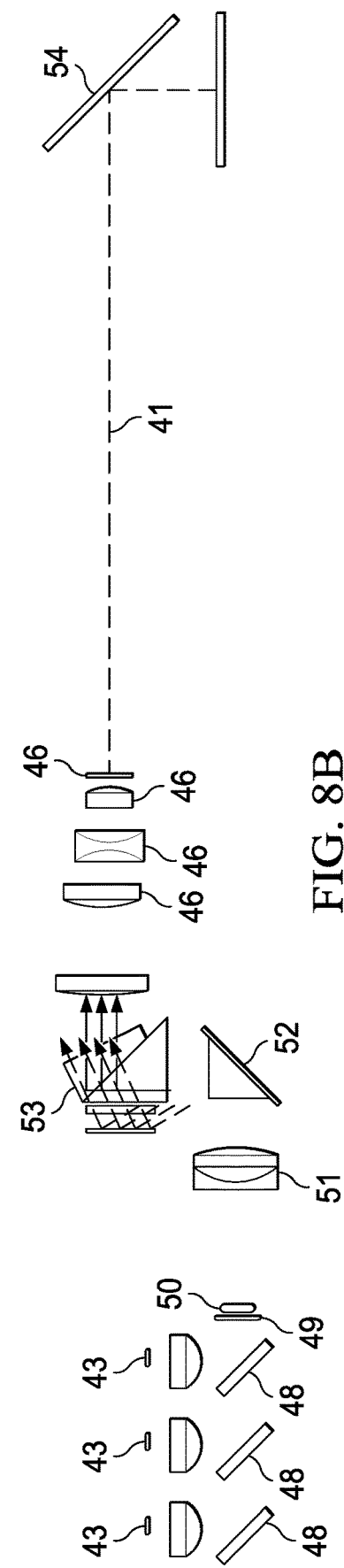
FIG. 8B is an elevation view of the optical system.

FIGS. 8A and 8B depict the scanner's optical system in additional detail. FIG. 8A is a plan view, and FIG. 8B is an elevation view. As best depicted in FIG. 8A, the scanner's optical system 40 is configured to include two (2) optical paths, namely, a laser projection path 41, and an optical imaging path 42. Generally, the laser projection path preferably comprises a sub-system of three (3) color (RGB) lasers 43, and a spatial light modulator [44] (e.g., the Texas Instruments DLP® Technology light modulator, element 18 in FIG. 4A) to project a structured laser light pattern and live view color illumination on the tooth surface. The optical imaging path 42 is a sub-system that comprises a high speed and high-resolution CCD (or CMOS) sensor 45 to capture the image of the laser light pattern projected on the tooth surface from a perspective view. The separation of the two optical paths (which are configured side-by-side as depicted) forms a triangulation between a projected laser light pattern and the CCD optical imaging such a 3D shape of the tooth surface can be determined based on well-known triangulation principles. Preferably, both the projecting lenses 46 and the imaging lenses 47 each include the same four lens group and are optimized for high resolution, color correction, and tele-centric rays in the imaging space. In addition to the three (3) color laser diodes 43, the laser projection sub-system includes laser collimating lenses 48, color combining filters 49, a micro-lens array homogenizer 50, a laser speckle reducer 51, an achromatic doublet lens 52, and a reflective TIR (Total Internal Reflection) prism 53 (as previously described). At the end of the scanner tip, the transmitted light is reflected off mirror 54.

Preferably, the depth of the field (approximately 15 mm) in the optical imaging path is designed based on controlling of aperture stop size and focal length. The depth of the field (e.g., approximately 15 mm) in the laser projection path is designed based on a slit aperture stop (as will be described in more detail below) to achieve sharp laser lines and bright laser output. The field of view (e.g., approximately 17 mm×13 mm) is designed based on the selected CCD sensor and spatial light modulator size, tip mirror size, optical magnification and total optical length. Preferably, a small imaging aperture stop and projection aperture stop located at the front of the optical system and without using any glass window, and preferably all of the lenses are attached to the main mechanical housing to avoid fogging in the optical path with the tip mirror, which is preferably heated.

Without intended to be limiting, representative optical design parameters of the scanner are as follows: effective focal length (26.6 mm), triangulation angle)(6.55°), magnification (1/3.6$^x$), field of view (17.6 mm×13.2 mm), CCD sensor size (4.736×3.552 mm with 7.4 µm pixel, 200 fps), spatial light modulator (0.3" with 10.6 µm pitch in column), color (3 lasers with RGB color), contrast (on and off mirror switching), uniformity (flat-top illumination with micro lens array).

Figure 9:
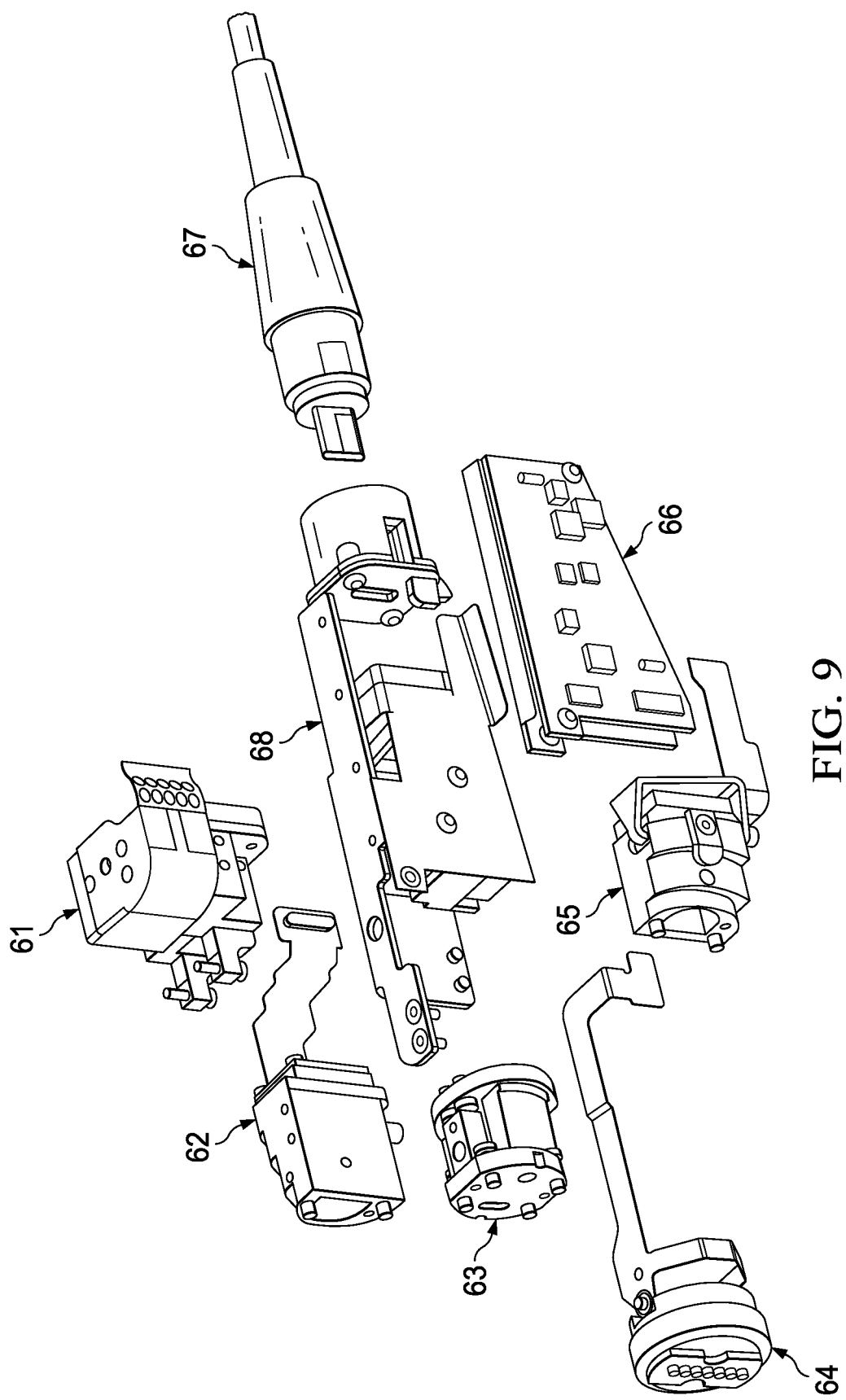
FIG. 9 depicts a component-specific view of a preferred embodiment of the scanner.

Referring now to FIG. 9, a component-specific view of a preferred embodiment of the scanner is shown in additional detail. The plastic case that houses these components is not shown. As depicted, in this embodiment the scanner 60 comprises despeckler module 61, projection module 62, lens tube module 63 (with the cat-eye slotted aperture), tip mount module 64, camera module 65, electronics module 66, data cable 67, and light engine module 68.

The cat-eye aperture of the lens tube module provides additional advantages. In operation, and as depicted in FIG. 8A, the light exiting from the TIR prism goes through the lens tube module (that supports the four lens projection system 46). The lens tube module includes the cat-eye (or "stop") aperture having a slotted shape. Advantageously, the slot is configured along the laser line direction, thereby allowing more laser power to go through the system. The narrow direction of the aperture produces sufficient depth of field for the thin and sharp laser lines. Preferably, the lens projection system 46 is identical to the adjacent imaging system 47, which is optimized for high resolution and high depth of field for 3D measurement. Typically, the imaging system has a stop aperture of circular shape. The four lens system is a tele-centric design in imaging space for improved transmission and detection.

Preferably, and with reference again to FIG. 1, the scanner tip 2 and data cable 3 are detachable and are replaceable components. The data cable 3 that attaches the scanner to a computer is a USB 3.0 data cable preferably attached to the remainder of the device by a bayonet lock style connector.

In operation, scanning software resident on an associated computer (e.g., desktop, laptop, or the like) extracts a 3D point cloud from the captured data, aligns the 3D point cloud to previously captured data, and renders to a display screen (or other output). This process is repeated as the user continues to scan. The system then allows the user to bring the restored anatomical data into a design tool. Through the use of the software, the user then designs a restoration (e.g., a crown) to fit the anatomical features.

Figure 10:
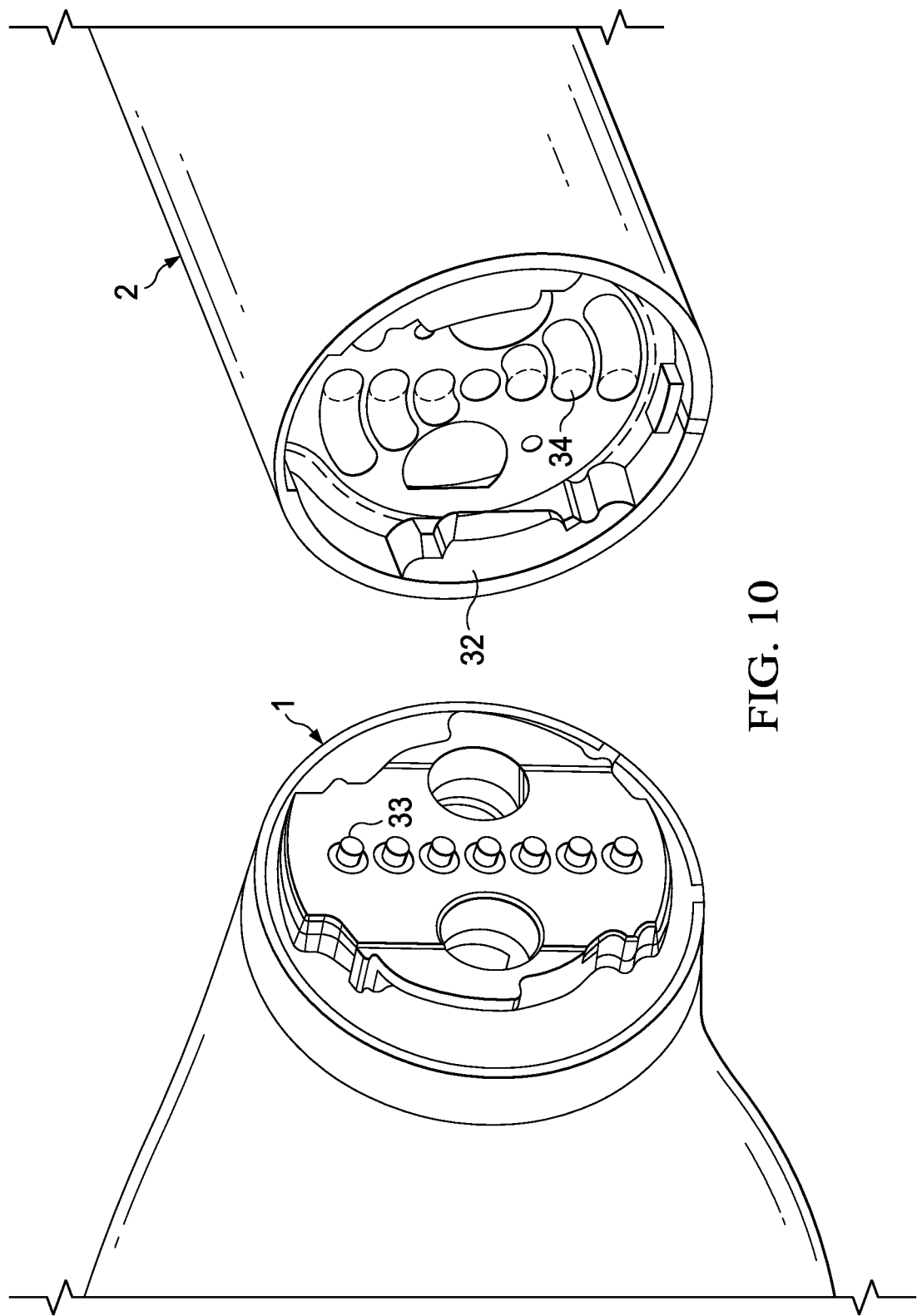
FIG. 10 depicts a twist lock mechanism for attaching the scanner tip to the scanner body.

Preferably, the scanner tip's mechanical design is a one-piece plastic housing, preferably with no external seams. It may also include an orientation marking to facilitate use. A mirror in the tip preferably is heated to prevent fogging, which would otherwise negatively impact the clinical experience. As depicted in FIG. 10, the tip 2 is attached to the scanner body 1 using a twist lock mechanism 32. By rotating the body relative to the tip, the tip can be removed for service or replacement. Electrical connectivity to the heated mirror is provided by a connector structure, which includes contacts 33 on the body, a contact pad 34 comprising a set of pogo pad contacts. The electrical connectivity provided by the contacts 33 includes power, communications (e.g., in one specific case I$^2$C), and safety.

Preferably, the RGB lasers in the scanner are color-balanced to produce a desirable image as is now described. In particular, the approach herein uses color calibration via laser emitter balancing. The following describes an approach to this calibration process.

Each laser has a specified frequency range (i.e. red, green or blue), and the pulse width or power of each emitter is adjustable. As used herein, an "emitter" refers to the LEDs or lasers that illuminate the scene, "emitter driver value" refers to the value (e.g., pulse width or other electrical power) that drives the apparent amplitude of the emitter, and a value "tRGB" is a desired or target mean RGB value of a calibration target. To carry out the calibration process, the wand is first placed on a color calibration target that is greyscale. A target RGB value for the resulting image is then set to tRGB. An emitter driver value in the middle of an allowed range (that is configurable) is then selected. A snapshot of the target is then taken and the mean RGB values collected. A determination is then made whether the mean RGB value is greater than tRGB, and the result is used as an initial condition for a binary search. The emitter driver values are then adjusted using a binary search until a delta between the mean RGB and tRGB is minimized. The resulting optimized emitter driver values are then used to drive the color frames of the scanner (i.e., during normal use). Preferably, tRGB is selected such that green and blue have much stronger components than red, as this reduces the amount of red scattering in the patient's mouth. In an alternative embodiment, in lieu of greyscale, different color spaces (e.g., HSL, HSV) may be used to drive the calibration.

According to another aspect, color uniformity correction may be carried out as follows. The scanner is first placed on a color calibration target that is greyscale. The scene is then illuminated, preferably based on the optimized emitter driver values as described above. The frame is then captured. Then, the frame is blurred, e.g., using an n×n kernel. For each pixel, a scale factor is the calculated. The scale factor is a value that maps an input RGB to a desired output RGB that is similar to rRGB. The scale factor image is then compressed (e.g., using OpenJPEG), which reduces grid compression artifacts while significantly reducing file size. This compressed file is then stored to the scanner. Upon the start of scanning, this scale factor image is multiplied by the incoming scanner image to correct uniformity errors. The scale factor image is calculated and used in a pair of equations, the first equation being S=T/I, derived during calibration (and assuming element-by-element arithmetic operations), where S is the scale factor image, I is the incoming image from the scanner, and T is the image with tRGB at every pixel; the second equation being O=S*I, which represents the output after calibration (i.e., during scanning), where S is the scale factor image, I is the incoming image from the scanner, and O is the output image displayed to the user.

According to a further aspect, the following describes an efficient way to reduce shadows due to laser emitters residing on a different path from the image sensor. In this aspect, a kd-tree is computed from the generated 3D model. For each vertex on the generated model, and using the kd-tree, a ray is cast from the vertex to an estimated camera position. The intersected result is then stored. The routine preferably uses an epsilon along the ray to assure that the ray is not intersecting a test vertex. Using the kd-tree, a ray also is cast from the vertex to the estimated laser illumination position, and the intersected result also is stored. An epsilon also is used along the ray to assure the ray is not intersecting the test vertex. The color from the live view image is looked up only if the camera ray and laser ray are not occluded by other geometry.

Typically, the frames used to capture the data for the 3D model are partially-illuminated frames. To facilitate the operation of the device and provide live video as feedback to the operator (as well as the 3D-computed data), typically the scanner uses a sequence of patterns throughout which full illumination frames are selectively interspersed. A full illumination frame involves all or substantially all lines being turned on, as compared to a partially-illuminated approach, wherein only some lines are projected. In a full illumination frame, in effect there is no pattern. The partially-illustrated frames provide the data from which the 3D coordinates of the surface are determined. A technique for rendering frames in this manner is described in U.S. Pat. No. 7,184,150, the disclosure of which is incorporated herein by reference. In contrast, the full illumination frames are used for texturing the 3D model generated by the partially-illuminated frame data. In one sequence, a first set (e.g., six) pattern frames are used, interspersed with a second set (e.g., three) illumination frames, for a sequence total of nine total CCD frames. A software traffic shaper is then used to separate captured frames in two streams, namely, a live preview stream, and a data processing stream from which the 3D model is generated. If necessary, e.g., for computational or storage efficiencies, the live preview stream can give up priority and drop some frames when the CPU work load exceeds a certain limit.

As noted above, the intra-oral scanner described herein may be provided as a standalone scanner, or as part of a CAD/CAM system. In one non-limiting implementation, the scanner is part of a CAD/CAM system that uses dental CAD software, such as E4D Design Center, executing on a laptop or desktop machine, optionally together with specialized milling machine hardware driven by machine control CAM software. The dentist first prepares a patient's damaged tooth anatomy (using standardized dental practices) to receive a dental restoration including, but not limited to, an inlay, an onlay, a veneer, a crown or a bridge. Once the preparation has been made, the dentist uses the scanner described and illustrated herein to capture a digital impression of a patient's dental anatomy. Once the digital impression has been captured the dentist is presented with an "initial proposal" restoration by the automated CAD software. This initial proposal preferably automatically selects an appropriate tooth anatomy, and it sizes it to fit onto the preparation and within the patient's existing "good" anatomy. This initial proposal is then customized by the dental professional, typically using specialized software tools to adjust and modify the design, with the goal of ultimately achieving an optimized design that fits into the patient's anatomy. Once the final 3D model of the tooth has been achieved, it is sent electronically to a milling machine (or third party), which then generates the actual restoration from the design.

The RGB lasers in the scanner may be selectively controlled (or turned off) to produce any particular color (e.g., blue, purple, etc.). In another embodiment, the particular color utilized for scanning is a function of the material to be scanned.

The scanner tip also may be customized as needed (e.g., to include additional devices or elements) depending on the scanning application. The electrical interface to the tip provides greater customization possibilities by providing power, communication, and safety to the tip designer.

Having described our invention, what we claim is as follows.

The invention claimed is:

1. An intra-oral scanner, comprising:
   a body;
   a tip attached to the body;
   a light engine module comprising light sources supported in a housing; and
   a projection module, the projection module comprising a light modulator, and a Total Internal Reflection (TIR) prism comprising a first and a second prism elements, the first prism element being a right angle-shaped prism having a TIR surface, and the second prism element being a wedge-shaped prism positioned adjacent the TIR surface, the first prism element configured to receive light generated by the light engine module, and to reflect the received light off the light modulator;
   wherein light that exits a surface of the light modulator at an angle greater than normal is transmitted through the first and the second prism elements out of the TIR prism, and light that exits the surface of the light modulator at an angle less than normal is reflected by the first element and not transmitted through the second element.

2. The intra-oral scanner as described in claim 1 wherein the light sources of the light engine module comprise a red (R) laser diode, a green (G) laser diode, and a blue (B) laser diode.

3. The intra-oral scanner as described in claim 1 further including a lens tube module comprising a magnification lens housing.

4. The intra-oral scanner as described in claim 3 wherein the magnification lens housing supports one or more projection lens that receive light that transmitted out of the TIR prism.

5. The intra-oral scanner as described in claim 4 wherein a surface of the magnification lens housing includes an elongated aperture, the aperture elongated along a direction of a set of lines of a light pattern to be transmitted from the scanner.

6. The intra-oral scanner as described in claim 1 further including a despeckler module downstream of the light engine module, the despeckler module comprising a despeckling element and a drive motor.

7. The intra-oral scanner as described in claim 6 wherein the despeckler element comprises a diffuser disk driven by the drive motor.

8. The intra-oral scanner as described in claim 6 wherein the despeckler module also includes a micro lens array configured as a light homogenizer to make laser patterns generated by the light engine more uniform.

9. The intra-oral scanner as described in claim 1 wherein the tip is seamless.

10. The intra-oral scanner as described in claim 2 further including an associated electronics module comprising software that executes a laser emitter balancing process with respect to a color calibration target to color calibrate the laser diodes in the light engine module.

11. The intra-oral scanner as described in claim 10 wherein the laser emitting balancing process captures an image from a greyscale target, sets a target RGB value for the image to a target mean RGB value, selects emitter driver values for the laser diodes within a configurable range, collects mean RGB values, and thereafter adjusts the emitter driver values until a difference between the mean RGB values and the target mean RGB value is minimized.

12. The intra-oral scanner as described in claim 1 wherein the scanner body supports (1) a laser projection sub-system comprising the light engine module and the projection module, and (2) an optics imaging sub-system comprising a CCD or CMOS sensor to capture an image reflected from a tooth surface, wherein at least a portion of the laser projection sub-system and the optics imaging sub-system are configured side-by-side to reduce a form factor of the scanner body.

13. The intra-oral scanner as described in claim 1 wherein the projection module also includes a tele-centric lens.

14. The intra-oral scanner as described in claim 2 further including a full spectrum mirror, a red passing and green reflecting dichroic filter, and a blue reflecting, red and green passing dichroic mirror adjacent the laser diodes.

15. The intra-oral scanner as described in claim 1 wherein the tip includes electrical connectivity to provide power to a heated mirror supported in the tip.

16. An intra-oral scanner, comprising:
- a scanner body;
- a tip attached to the scanner body;
- a laser projection sub-system;
- an optics imaging sub-system comprising a CCD or CMOS sensor, wherein at least a portion of the laser projection sub-system and the optics imaging sub-system are configured side-by-side to reduce a form factor of the scanner body;

the laser projection sub-system comprising:
- a light engine module comprising light sources supported in a housing that generates a projected image comprising a pattern of lines;
- a despeckler module comprising a despeckling element, and a micro lens array configured to homogenize lines within the pattern, the despeckler module receiving the projected image from the light engine module;
- a projection module that receives the pattern from the despeckler module and includes a light modulator and TIR prism to selectively transmit the pattern depending on an angle of incidence of the pattern relative to a surface of the TIR prism; and
- a lens tube module that receives the pattern transmitted through the TIR prism and includes a slotted aperture to increase depth-of-field for the pattern of lines.

17. The intra-oral scanner as described in claim 16 wherein the light sources of the light engine module comprises a red (R) laser diode, a green (G) laser diode and a blue (B) laser diode.

18. The intra-oral scanner as described in claim 17 wherein the red laser diode, the green laser diode, and the blue laser diode are color-calibrated.

19. The intra-oral scanner as described in claim 17 wherein the red laser diode, the green laser diode and the blue laser diode are activated either individually or in combination as a function of a material or surface geometry to be scanned.

* * * * *